(12) United States Patent
Awad et al.

(10) Patent No.: US 9,974,749 B2
(45) Date of Patent: May 22, 2018

(54) METHOD OF TREATING DIABETIC WOUNDS USING BIOSYNTHESIZED NANOPARTICLES

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Mai Abdelrahman Elobeid Wagealla, Riyadh (SA); Promy Virk, Riyadh (SA); Khalid Mustafa Osman Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 14/877,916

(22) Filed: Oct. 7, 2015

(65) Prior Publication Data

US 2017/0100338 A1    Apr. 13, 2017

(51) Int. Cl.
| | |
|---|---|
| *A61P 31/04* | (2006.01) |
| *A61K 33/30* | (2006.01) |
| *A61P 17/02* | (2006.01) |
| *A61K 9/16* | (2006.01) |
| *A61K 33/38* | (2006.01) |
| *A61K 33/24* | (2006.01) |

(52) U.S. Cl.
CPC .......... *A61K 9/1664* (2013.01); *A61K 9/1694* (2013.01); *A61K 33/24* (2013.01); *A61K 33/30* (2013.01); *A61K 33/38* (2013.01)

(58) Field of Classification Search
None
See application file for complete search history.

(56) References Cited

U.S. PATENT DOCUMENTS

| 9,428,399 B1 * | 8/2016 | Awad | C01G 9/02 |
| 2004/0062817 A1 * | 4/2004 | Peshoff | A61K 31/43 424/642 |
| 2010/0055138 A1 * | 3/2010 | Margulies | A61K 8/02 424/401 |
| 2013/0129618 A1 * | 5/2013 | Katti | A61K 41/00 424/1.29 |

FOREIGN PATENT DOCUMENTS

| IN | 2011CH01461 | * | 5/2011 |
| WO | WO 2013/176633 A1 | | 11/2013 |

OTHER PUBLICATIONS

Mishra (Diabetic delayed wound healing and the role of silver nanoparticles, Digest J Nanomater & Biostructures 3(2) 2008, pp. 49-54).*

Chen (Topical treatment with anti-oxidants and Au nanoparticles promote healing of diabetic wound through receptor for advance glycation end-products, Eur J Pharm Sci 47(5), 2012, pp. 875-883 (Abstract)).*
Aromal (Green synthesis of gold nanoparticles using Trigonella foenum-graecum and its size-dependent catalytic activity, Spectrochimica Acta Part A: Mol & Biomol Spectroscopy 97, 2012, pp. 1-5).*
Ibrahim (Anti-inflammatory and Antioxidant Activity of Solenostemma argel extract, vol. 7, Issue 4, Article1, International Journal of Pharmacognosy and Phytochemical Research, at http://ijppr.com/volume7issue4article1/, available online: Jun. 3, 2015).*
Elia (Green synthesis of gold nanoparticles using plant extracts as reducing agents, International Journal of Nanomedicine, 2014:9 4007-4021).*
Ahmed (A review on plants extract mediated synthesis of silver nanoparticles for antimicrobial applications: A green expertise, Journal of Advanced Research (2016) 7, 17-28).*
Gunasekaran et al., "Silver Nanoparticles as real Topical Bullets for Wound Healing," Journal of the American College of Clinical Wound Specialists, 2012, 3, pp. 82-96.
Mishra et al., "Diabetic Delayed Wound Healing and the Role of Silver Nanoparticles," Digest Journal of Nanomaterials and Biostructures, 2008, vol. 3, No. 2, pp. 49-54.
M.R. Farahpour et al., "Evaluation of the wound healing activity of an ethanolic extract of Ceylon cinnamon in mice", Veterinarni Medicina, vol. 57 (2012) (1), pp. 53-57.
M.R. Farahpour et al., "Evaluation of the wound healing activity of *Cinnamomum zeylanicum* extract on experimentally induced wounds in rats", African Journal of Biotechnology, vol. 11(84) (Oct. 2012), pp. 15068-15071.
S.A. Chen et al., "Topical treatment with anti-oxidants and Au nanoparticles promote healing of diabetic wound through receptor for advance glycation end-products", Eur J Pharm Sci 47(5), 2012, pp. 875-883 (Abstract only).
J.E. Kim et al., "Accelerated healing of cutaneous wounds using phytochemically stabilized gold nancparticle deposited hydrocolloid membranes", Miomater. Sci. 3 (2015) pp. 509-519 (Abstract only).

* cited by examiner

*Primary Examiner* — H. Sarah Park
(74) *Attorney, Agent, or Firm* — Richard C. Litman

(57) ABSTRACT

The method of treating diabetic wounds using biosynthesized nanoparticles includes administering an effective amount of silver and gold nanoparticles to a patient in need thereof. The silver and gold nanocomposite is prepared by 'biosynthesis", i.e., by providing a first aqueous solution of a noble metal salt or a noble metal oxide; providing a second solution of an aqueous plant extract, and combining the first solution and the second solution to produce a solution including nanoparticles of the noble metal. The second solution includes a plant extract obtained from *Solenostemma argel, Trigonella foenum-graecum* and *Cinnamomum cassia*. The metal salt can include silver nitrate ($AgNO_3$) and chloroauric acid ($HAuCl_4$). Nanoparticles of gold and nanoparticles of silver are prepared separately, and then mixed to obtain a composition containing a gold and silver nanocomposite.

4 Claims, 17 Drawing Sheets

METHOD OF TREATING DIABETIC WOUNDS USING BIOSYNTHESIZED NANOPARTICLES

BACKGROUND OF THE INVENTION

1. Field of the Invention

The present invention relates to wound treatment, and particularly to a method of treating diabetic wounds using biosynthesized nanoparticles.

2. Description of the Related Art

Diabetes is a condition that affects millions of people throughout the world. One of the adverse effects of diabetes is its influence on wound healing. Diabetes itself can cause wounds, such as foot ulcers and leg ulcers. However, even when the wound is not caused by diabetes, the diabetic condition still adversely affects wound healing.

For example, it is known that wounds take longer to heal in patients who have diabetes than in the non-diabetic patient. Diabetes causes poor circulation, reducing the flow of blood and oxygen to the wound. This impairs immune system response, as well as the flow of nutrition to healthy tissue surrounding the wound and the growth of new tissue. Diabetes may be accompanied by some degree of diabetic neuropathy, so that the patient is unable to feel the progress of healing or the development of problems in the area surrounding the wound. Finally, diabetes is known to be accompanied by an increased risk of infection during wound healing.

In view of the foregoing, many efforts have been made to find forms of treatment that accelerate wound healing in the diabetic patent and that reduce or ameliorate the adverse effects described above, although none have proven entirely satisfactory. Thus, a method of treating diabetic wounds using biosynthesized nanoparticles solving the aforementioned problems is desired.

SUMMARY OF THE INVENTION

The method of treating diabetic wounds using biosynthesized nanoparticles includes administering an effective amount of silver and gold nanocomposite to a patient in need thereof. The silver and gold nanocomposite are prepared by 'biosynthesis", i.e., by providing a first aqueous solution of a noble metal salt or a noble metal oxide; providing a second solution of an aqueous plant extract, and combining the first solution and the second solution to produce a solution including nanocomposite particles of the noble metal or metal oxide nanoparticles. The second solution includes a plant extract obtained from *Solenostemma argel*, *Trigonella foenum-graecum* and *Cinnamomum cassia*. The metal salt can include silver nitrate ($AgNO_3$) and chloroauric acid ($HAuCl_4$). Nanoparticles of gold and nanoparticles of silver are prepared separately, and then mixed to obtain a composition containing both gold and silver nanocomposite.

Administration of the gold and silver nanocomposite by topical application of the treatment was followed on the cutaneous diabetic wounds at a dosage of 400 mg/kg body weight, which resulted in improved wound healing in the diabetic patient.

These and other features of the present invention will become readily apparent upon further review of the following specification and drawings.

BRIEF DESCRIPTION OF THE DRAWINGS

FIG. 7 FIG. 1 is a Zetasizer spectrum showing the average particle size of silver/gold nanoparticles biosynthesized using *Cinnamomum cassia* extract.

Similar reference characters denote corresponding features consistently throughout the attached drawings.

DETAILED DESCRIPTION OF THE PREFERRED EMBODIMENTS

Figure 1:
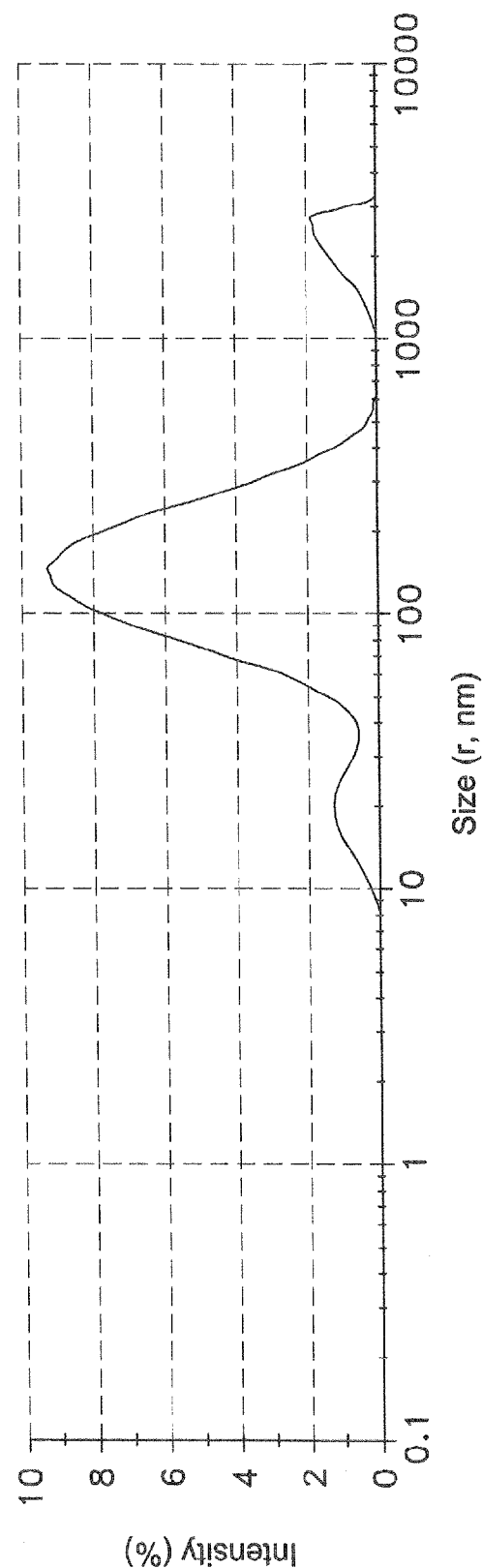
FIG. 1 is a Zetasizer spectrum showing the average particle size of silver/gold nanoparticles biosynthesized using *Solenosstemma argel* extract.

The method of treating diabetic wounds using biosynthesized nanoparticles includes administering an effective amount of silver and gold nanocomposite particles to a patient in need thereof. The silver and gold nanocomposite particles are prepared by "biosynthesis", i.e., by providing a first aqueous solution of a noble metal salt or a metal oxide; providing a second solution of an aqueous plant extract, and combining the first solution and the second solution to produce a solution including nanoparticles of the noble metal. The second solution includes a plant extract obtained from *Solenostemma argel*, *Trigonella foenum-graecum* and *Cinnamomum cassia*. The metal salt can include silver nitrate ($AgNO_3$) and chloroauric acid ($HAuCl_4$). Nanoparticles of gold and nanoparticles of silver are prepared separately, and then mixed to obtain a composition containing particles of a gold and silver nanocomposite.

In more detail, a method of synthesizing nanoparticles using a plant extract can comprise providing a first solution comprising a metal salt or a metal oxide; providing a second solution comprising a plant extract; and combining the first solution and the second solution to produce a nanoparticle solution including metal nanocomposite particles or metal oxide nanoparticles. Combining the first solution and the second solution may comprise mixing the first solution with the second solution at a temperature of about 20° C. to about 40° C. for about ten minutes to about fifteen minutes. The second solution may include an extract obtained from plants consisting of *Solenostemma argel*, *Trigonella foenum-graecum* and rods of *Cinnamomum cassia*. The metal salt can be silver nitrate ($AgNO_3$) or Chloroauric acid ($HAuCl_4$), and the metal oxide nanoparticle may be zinc oxide (ZnO). The metal or metal oxide nanoparticles may have a mean diameter in the range of from about 1 nm to about 100 nm, and may have one or more shapes selected from the group consisting of spherical-shaped, spheroidal-shaped, elongated/spherical shaped, rod-shaped and facet shaped.

The method also includes improving wound healing in diabetics, comprising the step of administering an effective amount of nanoparticle synthesized by the above green method, wherein the nanoparticles are administered by topical application of the treatment was followed on the cutaneous diabetic wounds, topically or intravenously. The therapeutically effective amount can range from 10 ng/day/kg body weight to 500,000 ng/day/kg body weight, but is preferably about 400 mg/kg of body weight.

As used herein the term "nanoparticle" or "nanocomposite" refers to a particle or composites having at least one dimension sized between 1 and 100 nanometers.

The following examples will further illustrate the synthetic processes of making the green nanoparticle and the nanocomposite.

Example 1

Synthesis of Silver and Gold Nanoparticles

For the synthesis of the silver/gold nanocomposite, the reagents were used as received without further purification. The silver nitrate and chlrouric acid were obtained from Techno Pharmchem and Loba Chemie, India while the powdered rods of Cinnamon cassia were obtained from the local market. About 3 g of the leaves of *Solenostemma argel* or the seeds of *Foenum-graecum* or the rods of the plant *Cinnamomum cassia* rods was soaked in 90 mL of boiled distilled water overnight. The extracts were filtered, and the filtrates were immediately used for preparation of the nanoparticles. About 1 mM Silver nitrate ($AgNO_3$) and 1 mM Chloroauric acid ($HAuCl_4$) were dissolved in 50 ml of distilled water individually under vigorous stirring at 80° C. for 5 minutes. Then 5 ml of *Solenostemma argel* or *Foenum-graecum* seeds or *Cinnamomum cassia* extract was added to the solutions of both silver nitrate and Chloroauric acid separately. A change in color of the colloidal solutions occurred, which confirmed the reduction of $Ag^+$ ions or the $Au^{3+}$ ions and the formation of silver nanoparticles and gold nanoparticles. Then the solution of silver nanoparticles was mixed with the solution of gold nanoparticles to obtain final solution an aqueous solution containing both silver and gold nanocomposite. The mixture of gold and silver nanocomposite solutions for each plant extract were isolated and incubated at room temperature until used.

Figure 2A:
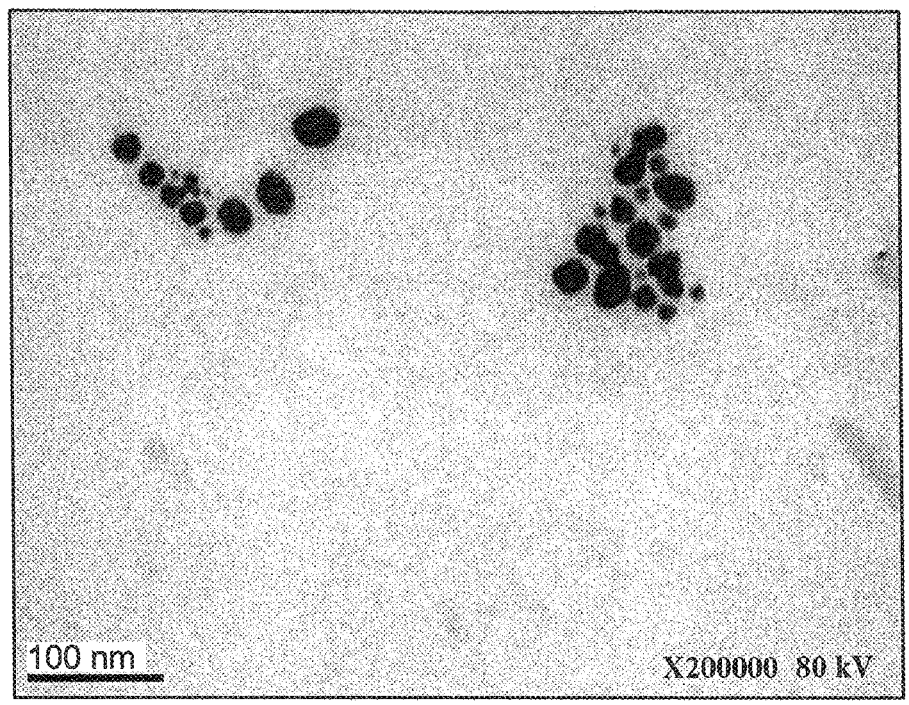
FIGS. 2A and 2B are transmission electron microscopy (TEM) micrographs of silver and gold nanoparticles biosynthesized using *Solenosstemma argel* extract.
Figure 2B:
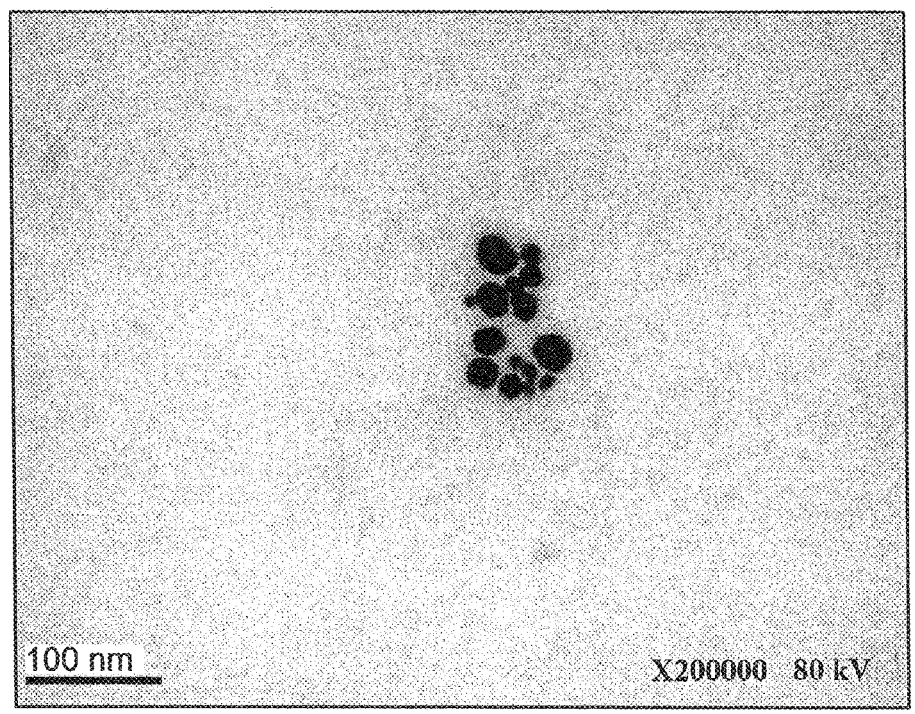

FIG. 1 shows the Zetasizer measurement the average size of silver/gold nanoparticles synthesized by the extract of *Solenostemma argel* (HR). Three peaks are observed corresponding to Peak 1 with a diameter of 157.4 nm, Peak 2 with a diameter of 20.47 nm and Peak 3, with a diameter of 2217 nm. FIGS. 2A and 2B show transmission electron microscopy (TEM) micrographs of the cluster of noble metal nanoparticles (silver and gold) synthesized by the extract of *Solenostemma argel*. Particles of various sizes and dimensions are observed. Energy Dispersive Spectrometer (EDS) studies indicated that the nanoparticles comprise 32.34% by weight of silver and 28.58% by weight of gold.

Figure 5:
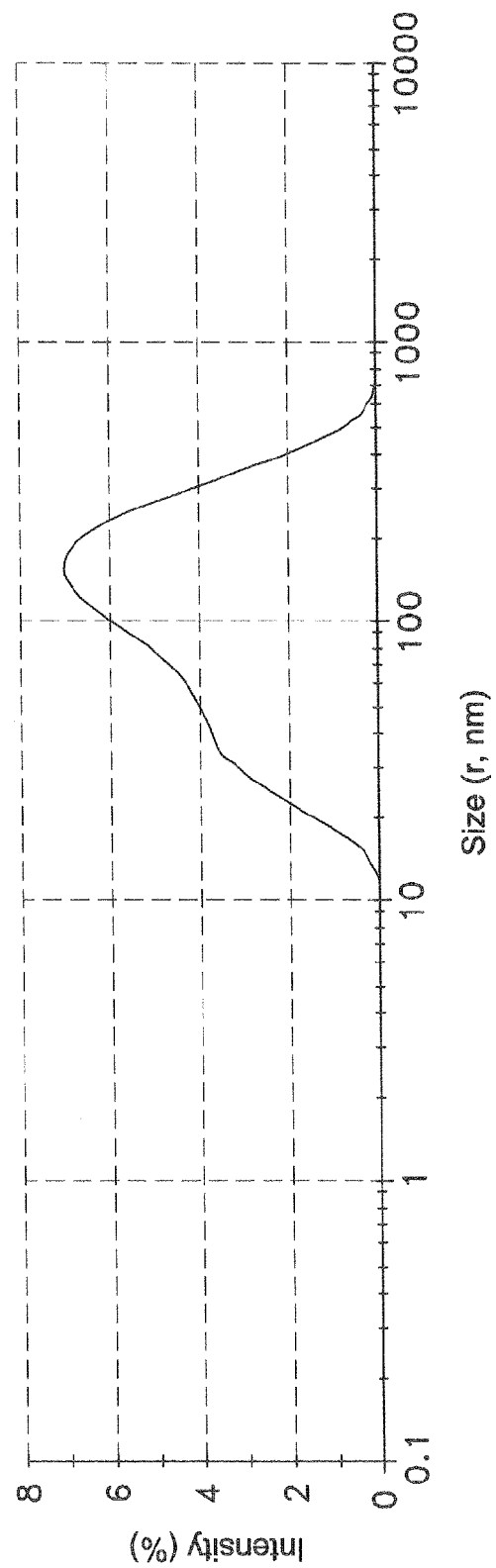
FIG. 5 is a Zetasizer spectrum showing the average particle size of silver/gold nanoparticles biosynthesized using *Trigonella foenum-graecum* extract.
Figure 6A:
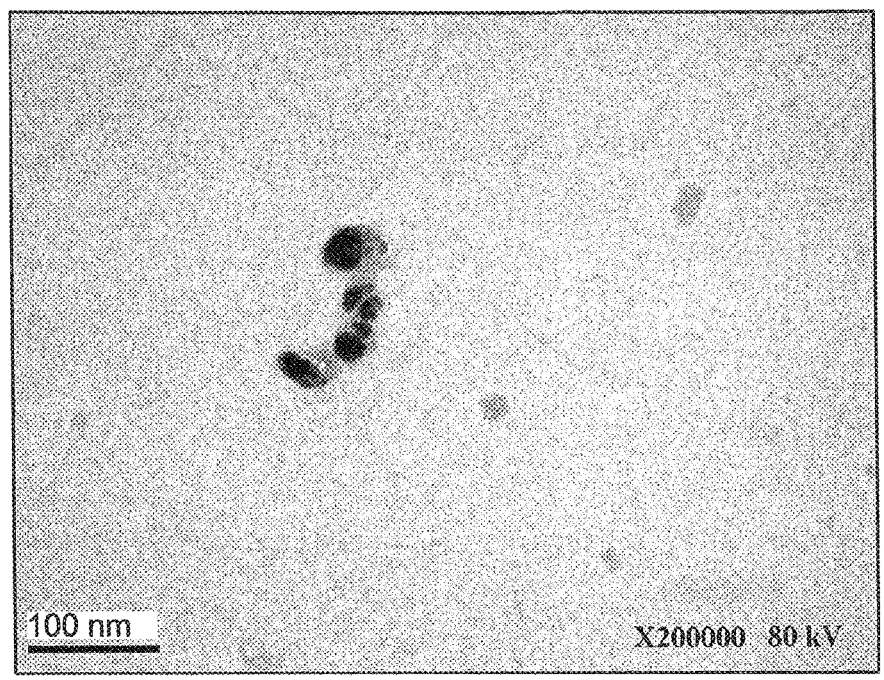
FIGS. 6A and 6B are TEM micrographs of silver/gold nanoparticles biosynthesized using *Trigonella foenum-graecum* extract.
Figure 6B:
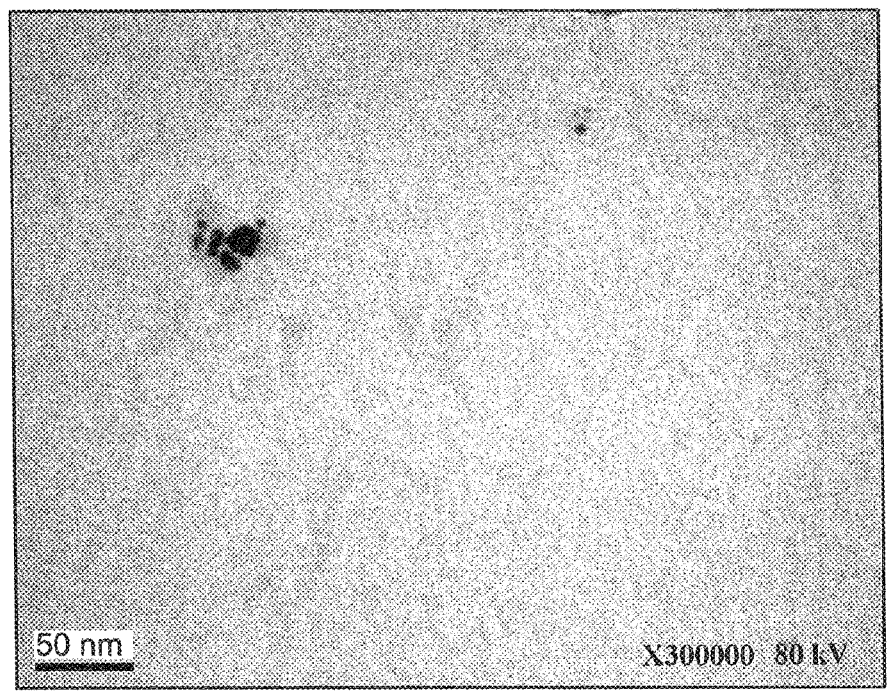

FIG. 5 shows the Zetasizer measurement of the average size of silver/gold nanoparticles synthesized by the extract of *foenum-graecum*. A broad peak is observed with a diameter of 139.7 nm. FIGS. 6A and 6B show TEM micrographs of the silver/gold nanoparticles synthesized by the extract of *foenum-graecum*, showing particles of various sizes.

Figure 7:
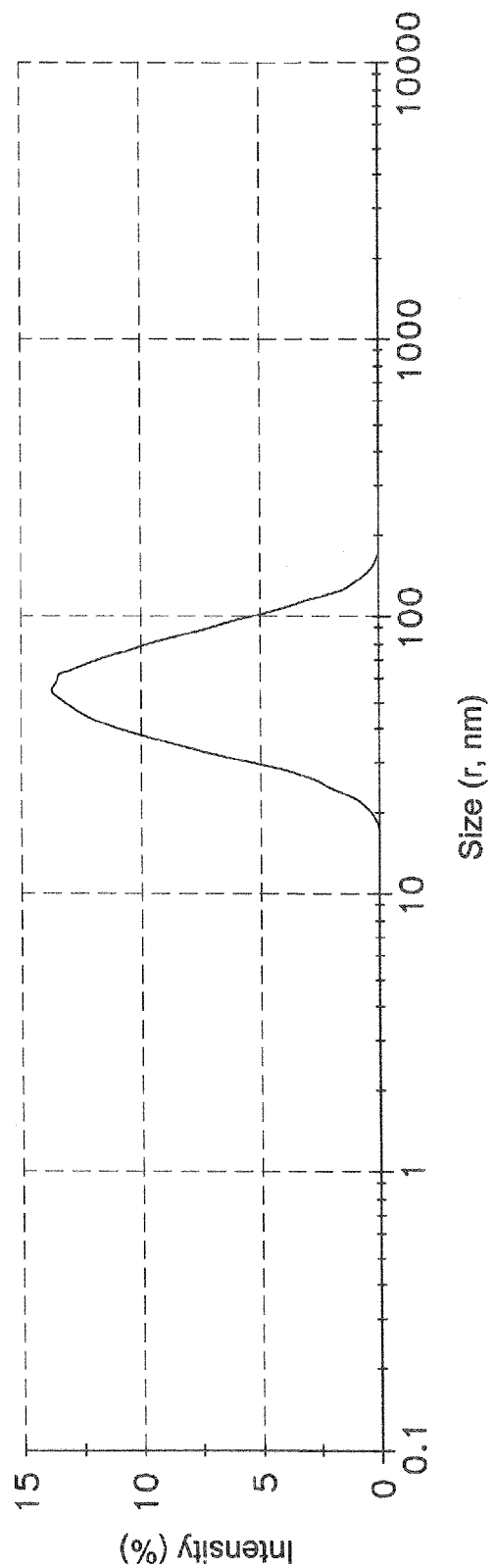
Figure 8A:
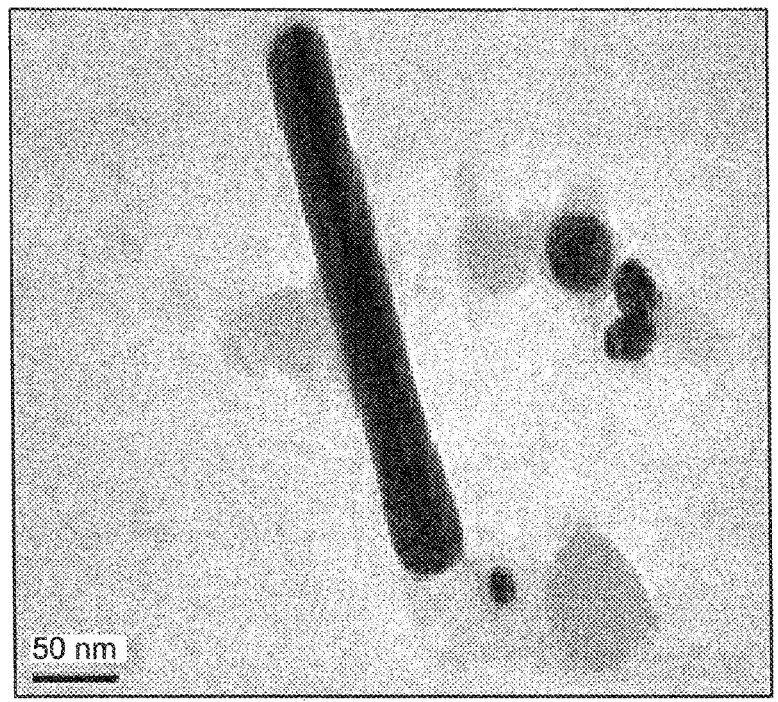
FIGS. 8A, 8B, 8C and 8D are TEM micrographs of silver/gold nanoparticles biosynthesized using *Cinnamomum cassia* extract.
Figure 8B:
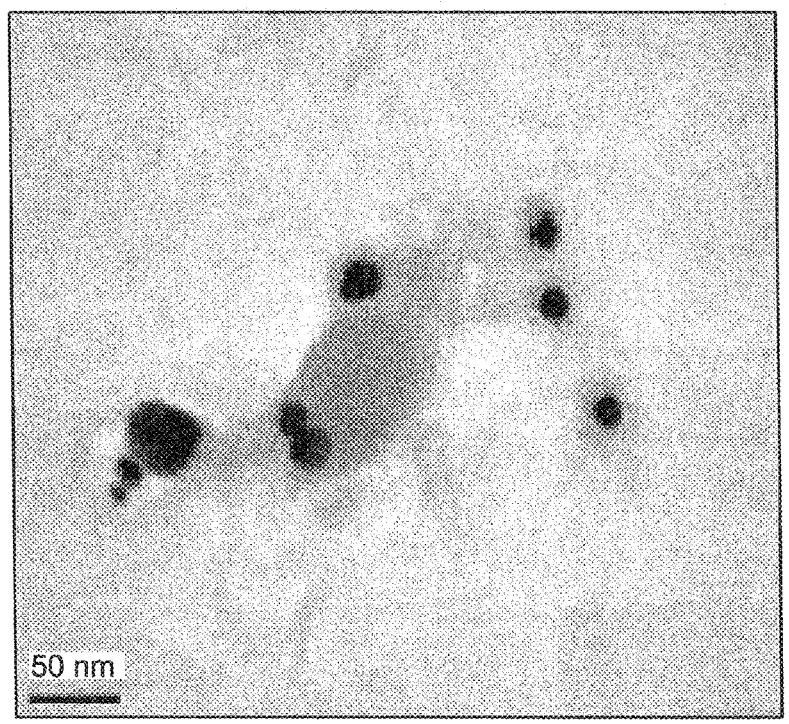
Figure 8C:
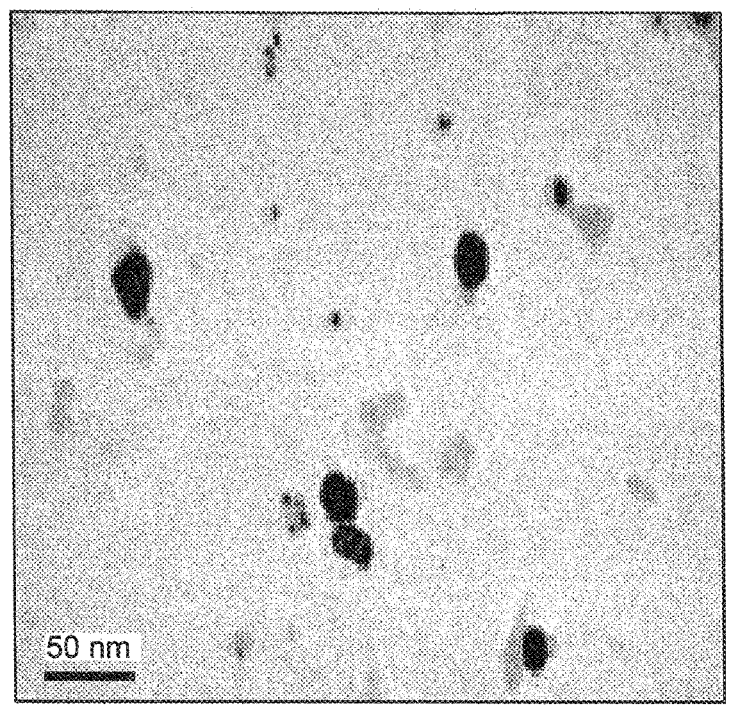
Figure 8D:
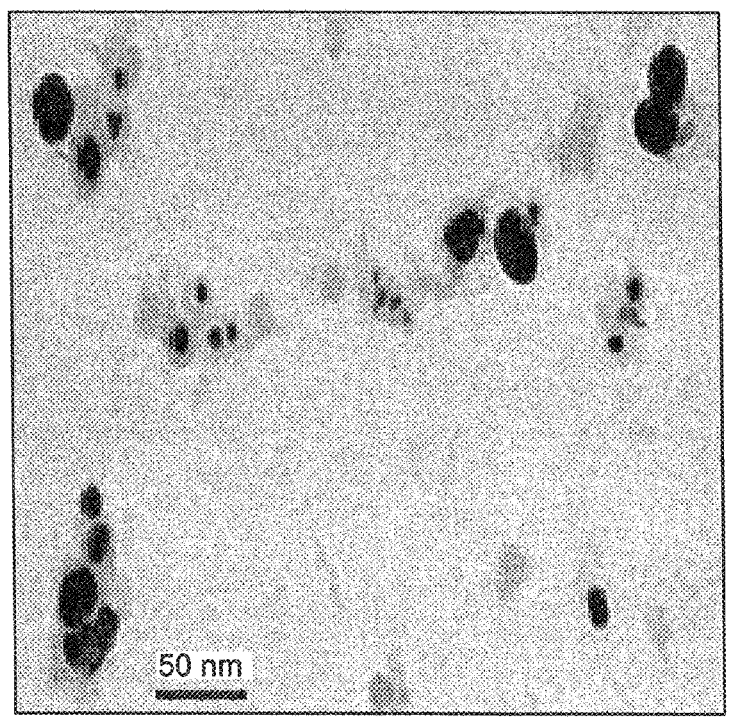

FIG. 7 shows the Zetasizer measurement of the average size of silver/gold nanoparticles synthesized by the extract of the extract of *Cinnamomum cassia*. A single peak is observed, corresponding to Peak 1 with a diameter of 58.73 nm. FIGS. 8A through 8D show TEM micrographs of the silver/gold nanoparticles synthesized by the extract of the extract of *Cinnamomum cassia*. As can be seen in the micrographs, the nanoparticles have one or more shapes selected from the group consisting of spherical-shaped, spheroidal-shaped, elongated/spherical shaped, rod-shaped and faceted shaped. The EDS results show that the nanoparticles synthesized according to this method result in 97.32% by weight of silver or 98.51 percent atomic weight, 2.68% by weight of gold or 1.49% by atomic weight present in the green silver/gold nanoparticle suspension.

Example 2

Synthesis of Zinc Oxide Nanoparticles

About 0.1 M zinc acetate (Merck, 99% purity) or 0.5M zinc nitrate was dissolved in 50 ml extracts of the leaves of *Solenostemma argel* (HR) or the seeds of *Trigonella foenum-graecum* (H) or the rods of the plant *Cinnamomum cassia* (JF) until it reduced to colored paste. Then the paste was dried to obtain colored powder of ZnO nanoparticles.

Figure 3:
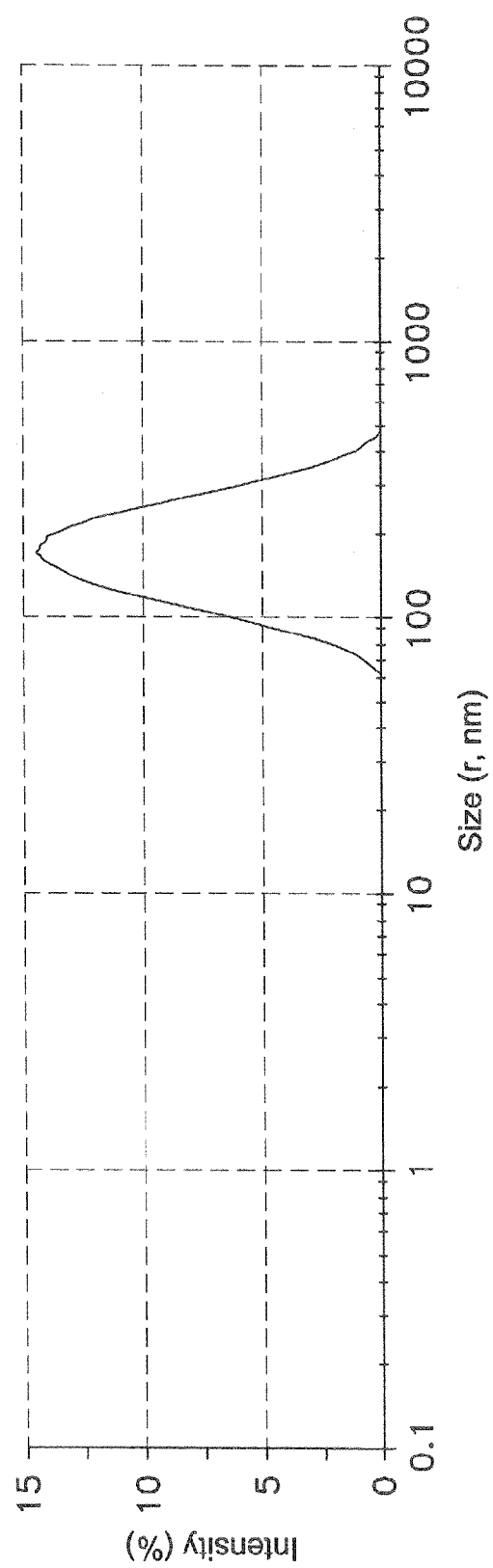
FIG. 3 is a Zetasizer spectrum showing the average particle size of zinc oxide (ZnO) nanoparticles biosynthesized using *Solenosstemma argel* extract.

FIG. 3 represents a graph of the average size distribution by intensity of zinc oxide (ZnO) nanoparticles prepared according to the above procedure using the extract of *Solenostemma argel* (HR). A single peak is observed corresponding to the diameter of 184.1 nm.

Figure 4A:
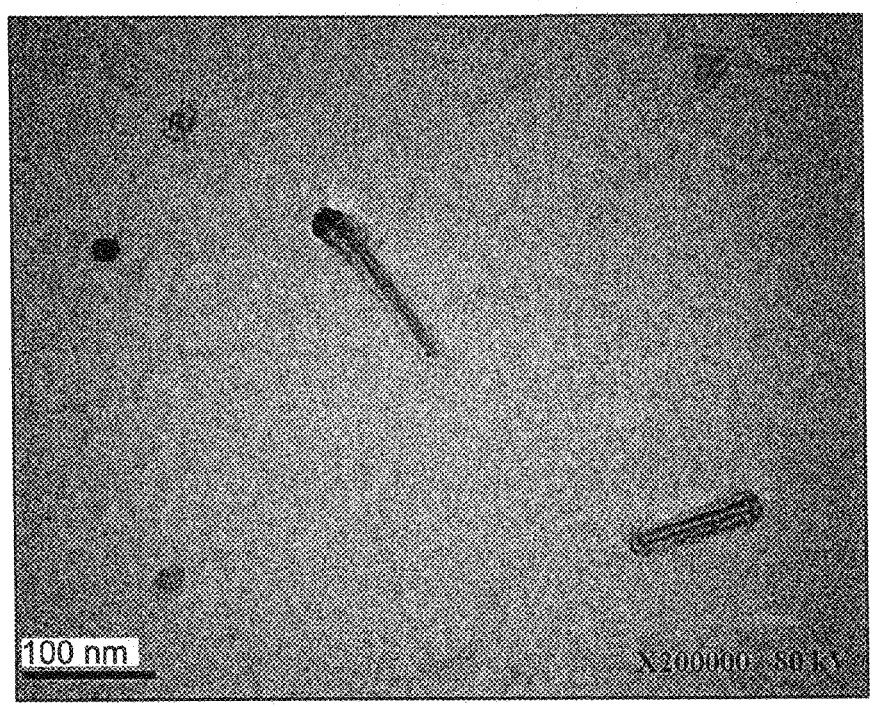
FIGS. 4A and 4B are TEM micrographs of ZnO nanoparticles biosynthesized using *Solenosstemma argel* extract.
Figure 4B:
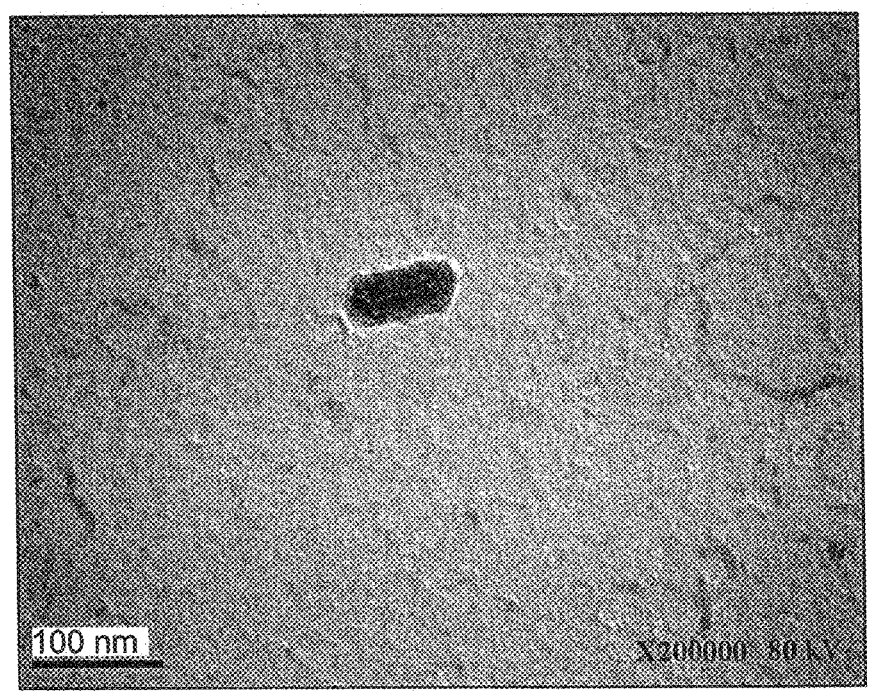

FIGS. 4A and 4B represent transmission electron microscopy (TEM) micrographs of zinc oxide nanoparticles synthesized using the extract of *Solenostemma argel* (HR).

Figure 9:
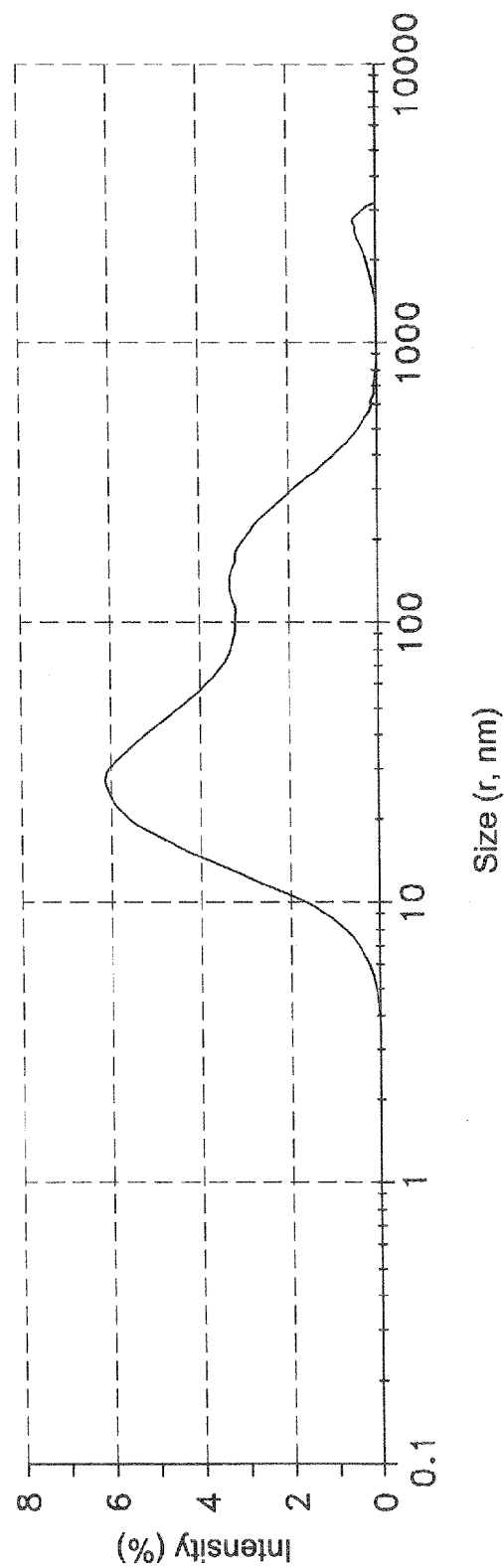
FIG. 9 is a Zetasizer spectrum showing the average particle size of zinc oxide (ZnO) nanoparticles biosynthesized using *Cinnamomum cassia* extract.
Figure 10A:
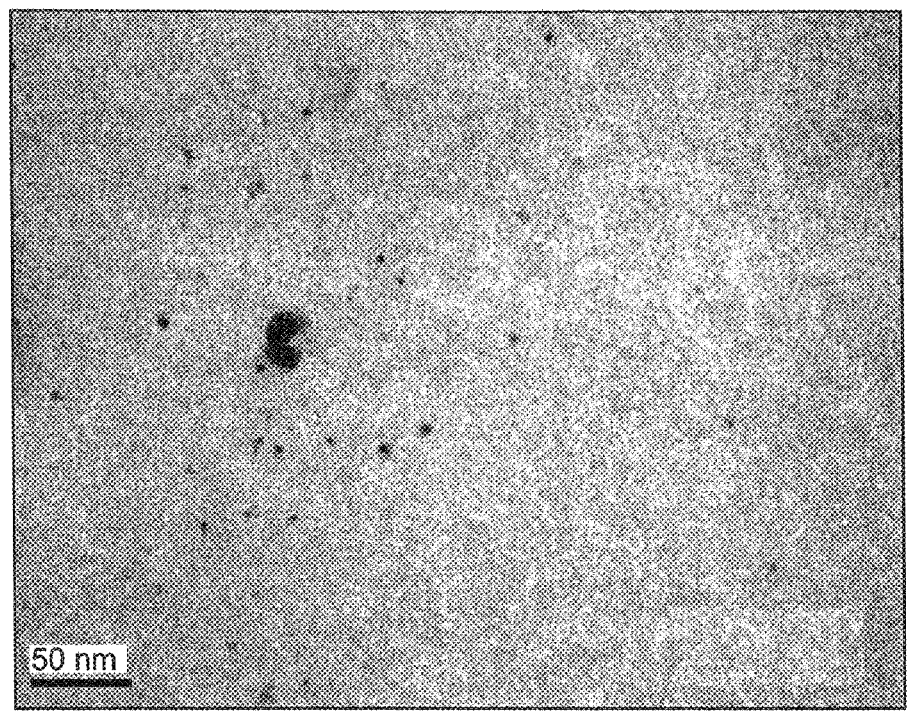
FIGS. 10A and 10B are TEM micrographs of the ZnO nanoparticles synthesized by the extract of *Cinnamomum cassia*.
Figure 10B:
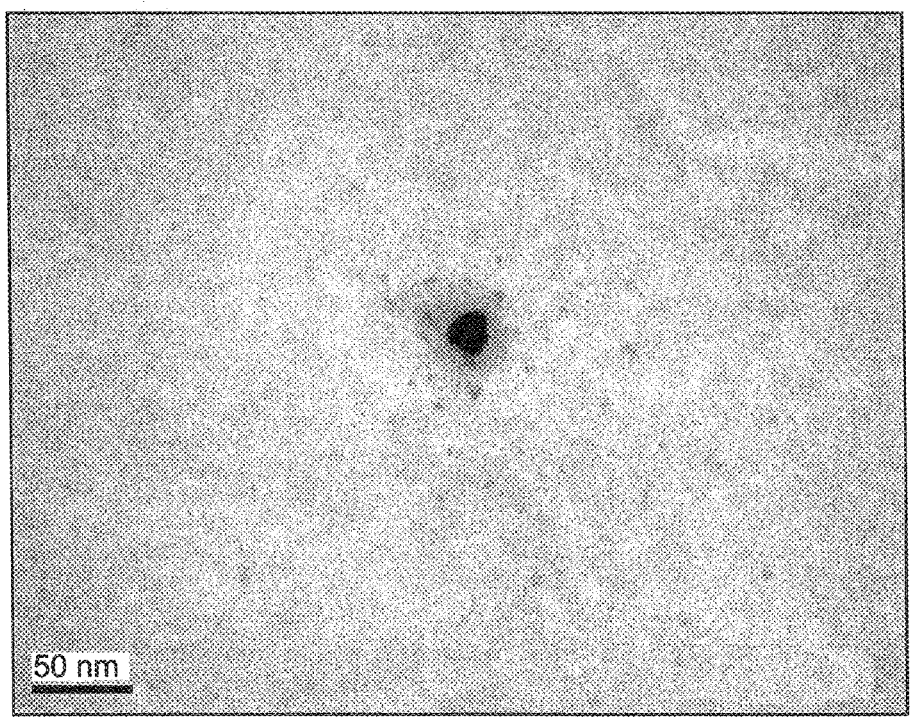

FIG. 9 presents a graph of the average size distribution by intensity zinc oxide (ZnO) nanoparticles prepared according to the above procedure using *Cinnamomum cassia*. Three peaks are observed corresponding to Peak 1 with a diameter of 36.41 nm, Peak 2 with a diameter of 196.4 nm and Peak 3, with a diameter of 2411 nm. FIGS. 10A and 10B present transmission electron microscopy (TEM) micrographs of zinc oxide (ZnO) nanoparticles synthesized using *Cinnamomum cassia*. The EDS results show that the nanoparticles synthesized according to this method result in 32.01% by weight of Zinc, 32.60% by weight of oxygen, and 35.39% by weight of carbon.

Example 3

Diabetes Studies Using the Synthesized Nanoparticles

Figure 11:
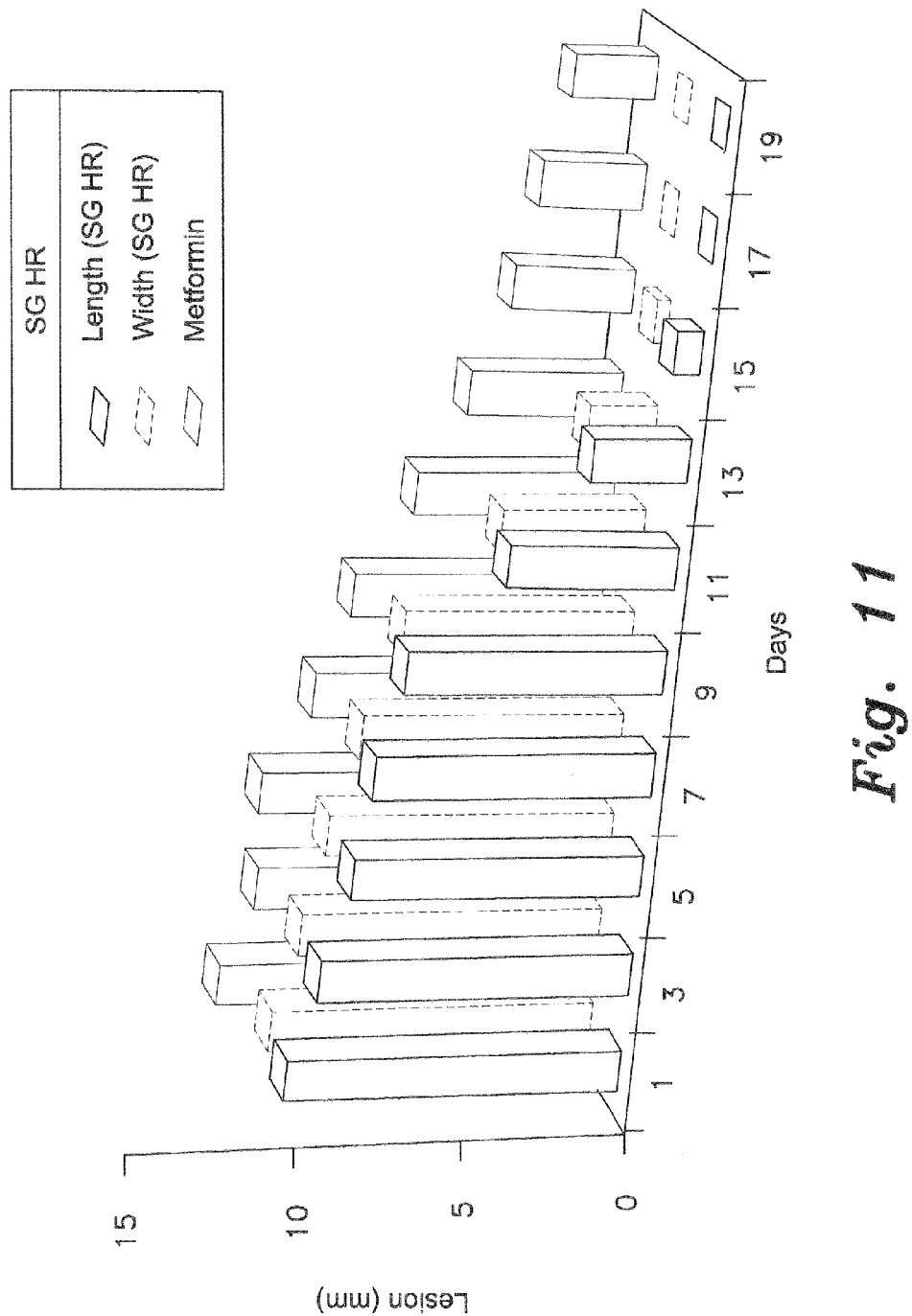
FIG. 11 is a chart comparing lesion size (mm) as a function of days for metformin, and for silver/gold nanocomposite biosynthesized using *Solenostemma argel* extract.
Figure 12:
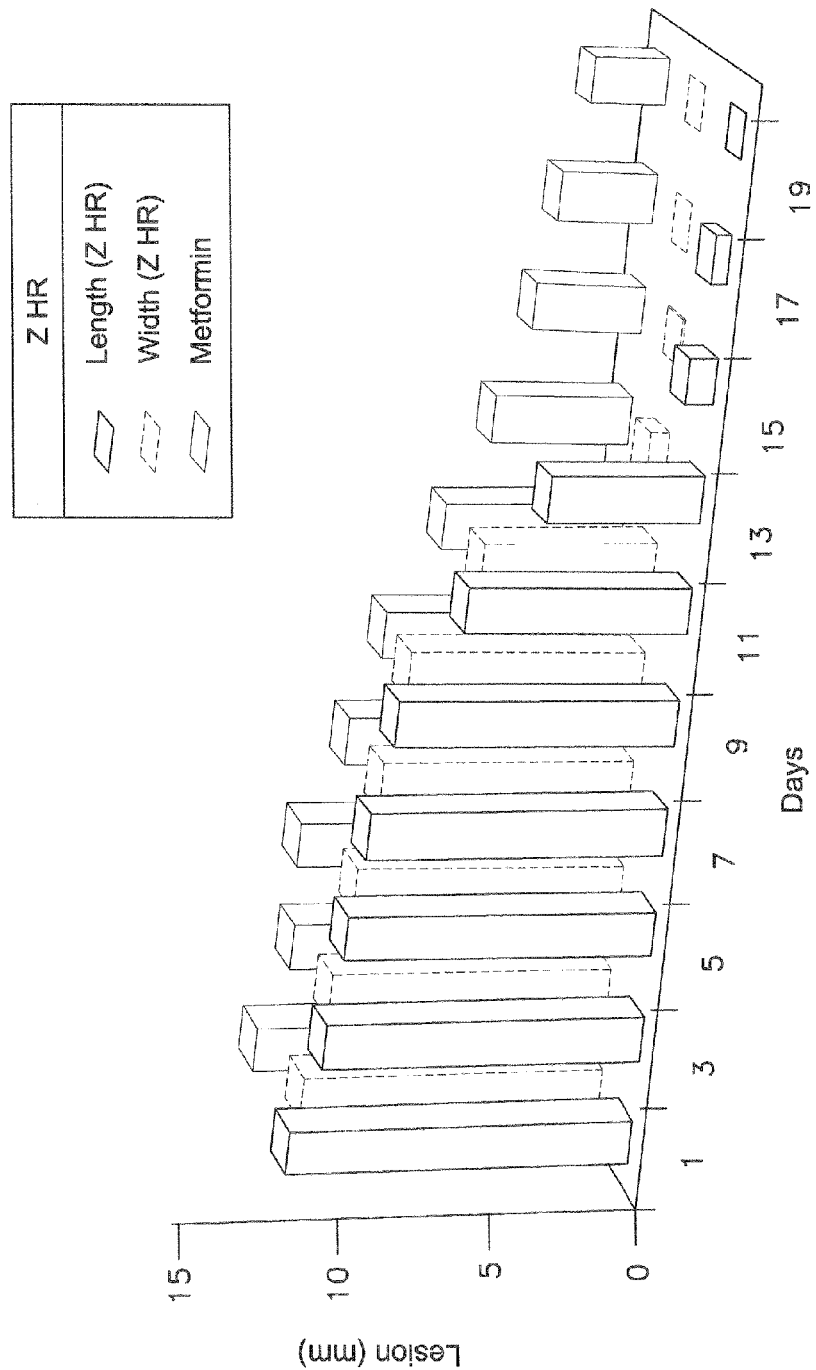
FIG. 12 is a chart comparing lesion size (mm) as a function of days for metformin, and for zinc oxide nanoparticles biosynthesized using *Solenostemma argel* extract.
Figure 13:
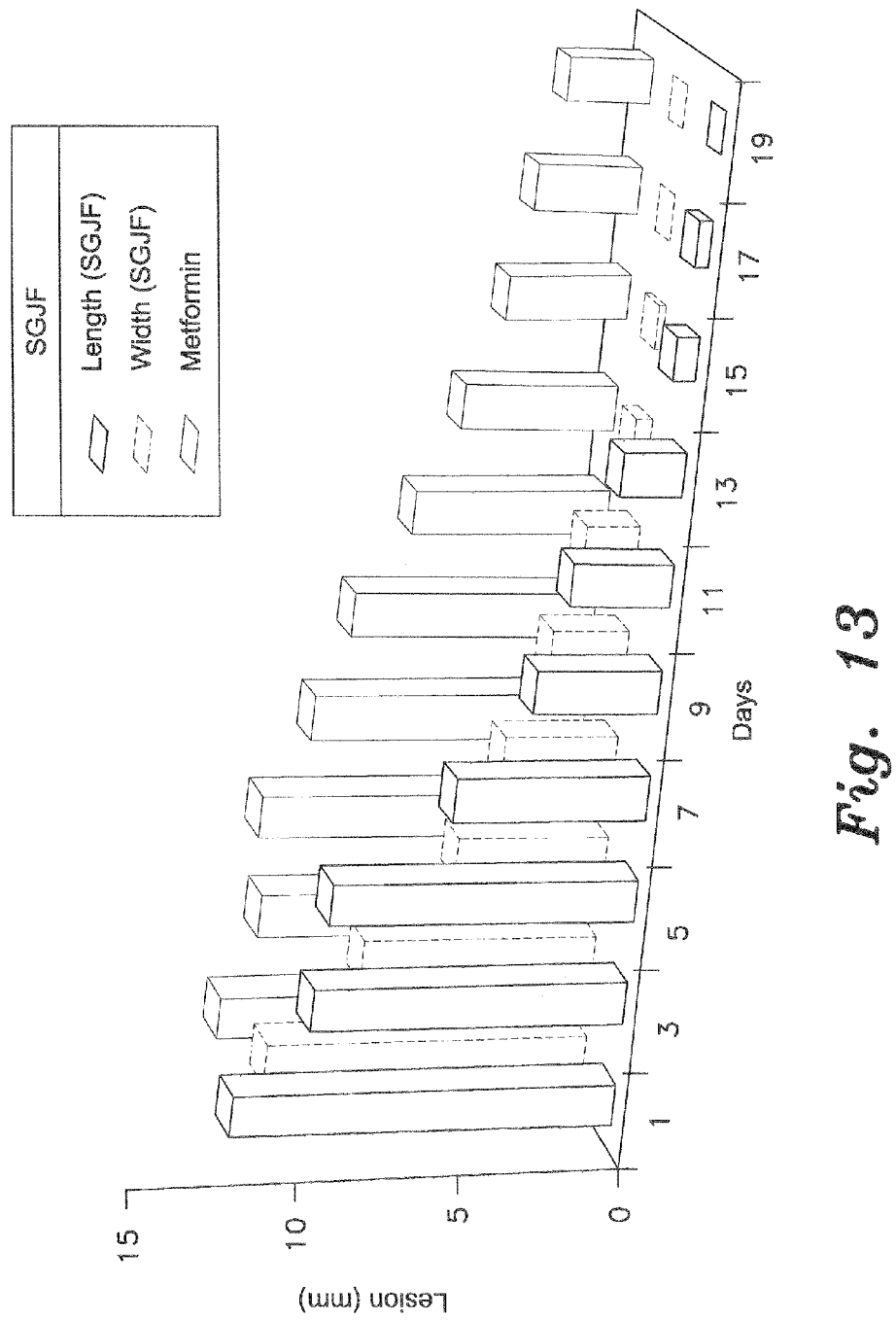
FIG. 13 is a chart comparing lesion size (mm) as a function of days for metformin, and for silver/gold nanocomposite biosynthesized using *Cinnamomum cassia* extract.
Figure 14:
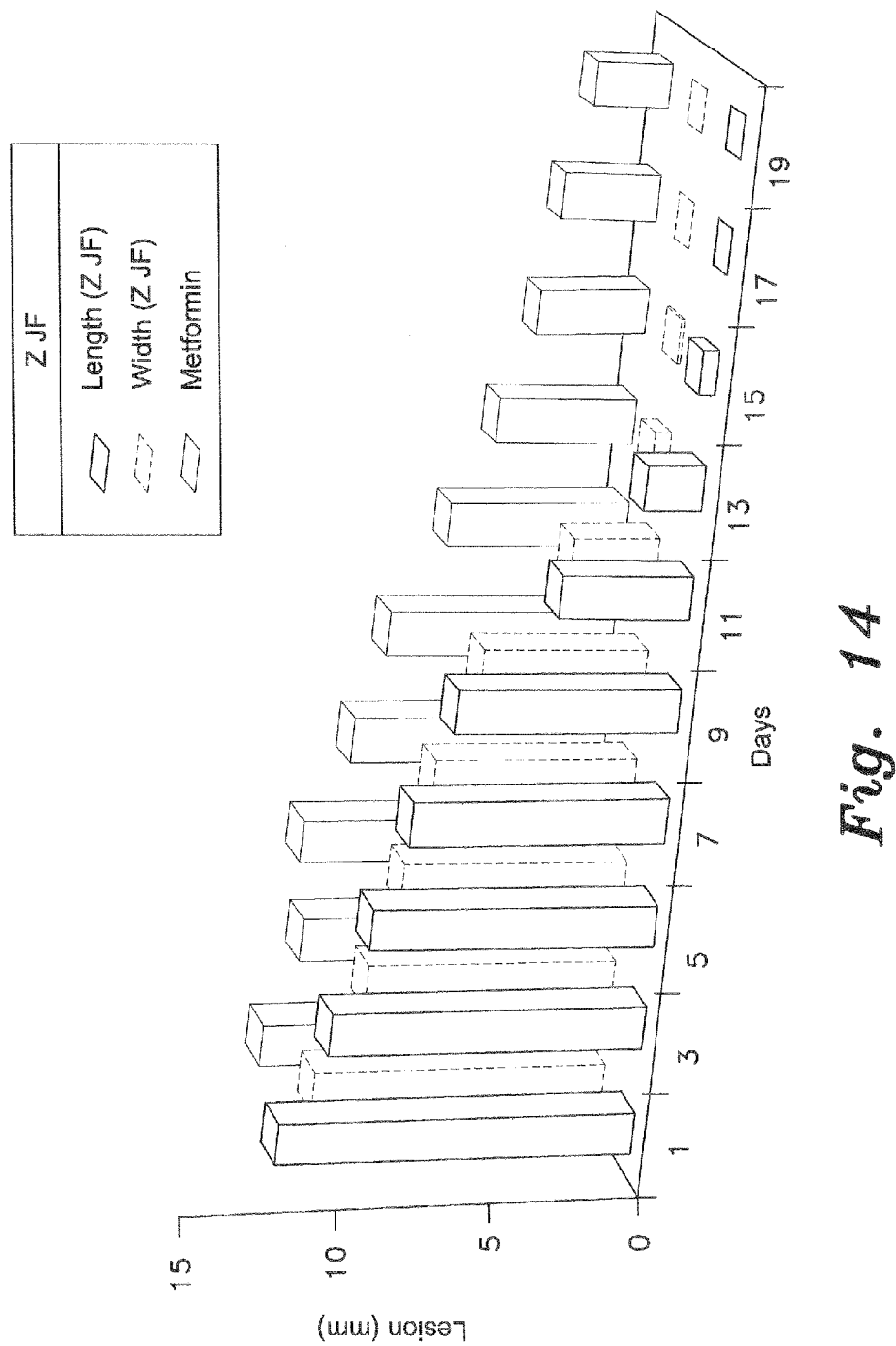
FIG. 14 is a chart comparing lesion size (mm) as a function of days for metformin, and for zinc oxide nanoparticles biosynthesized using *Cinnamomum cassia* extract.
Figure 15:
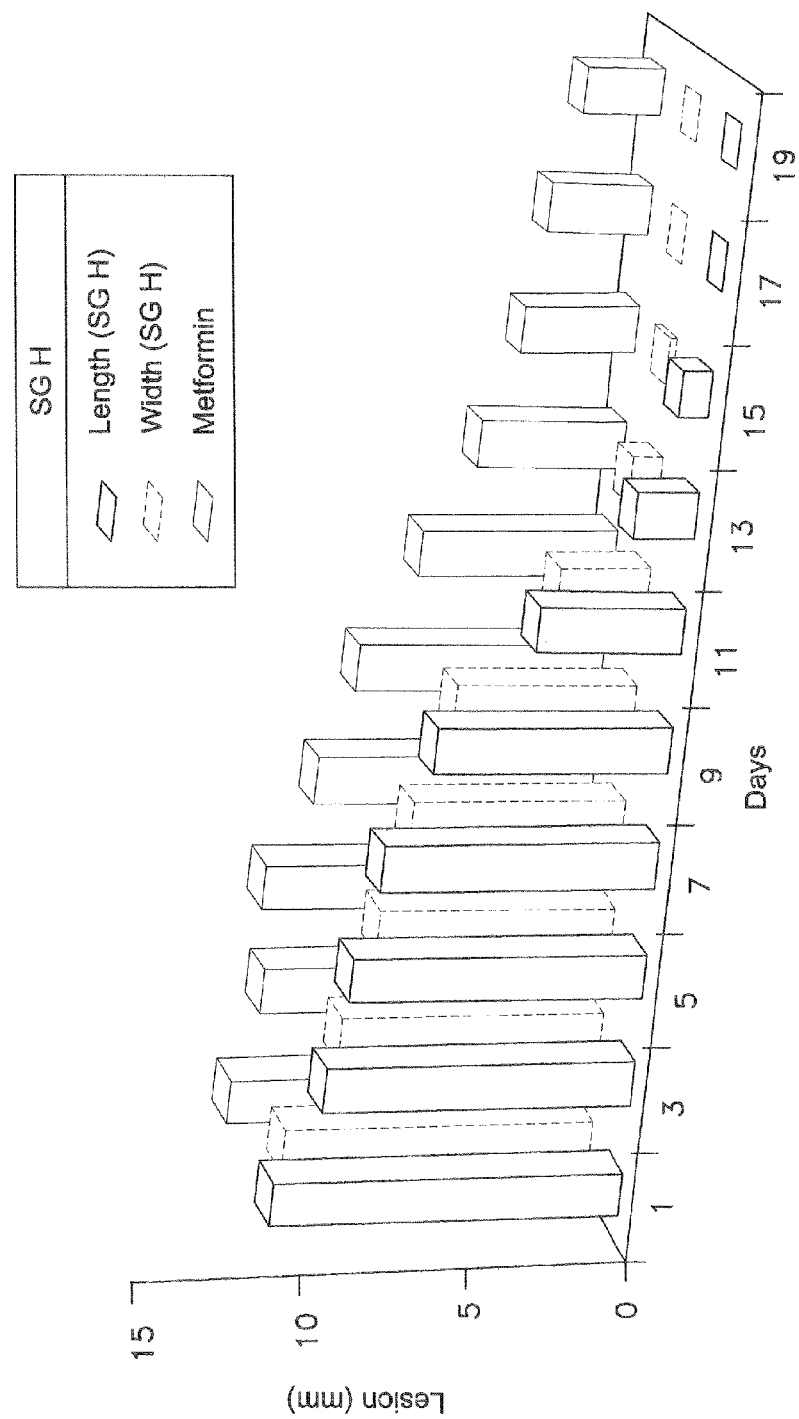
FIG. 15 is a chart comparing lesion size (mm) as a function of days for metformin, and for silver/gold nanocomposite biosynthesized using *Trigonella foenum-graecum* extract.
Figure 16:
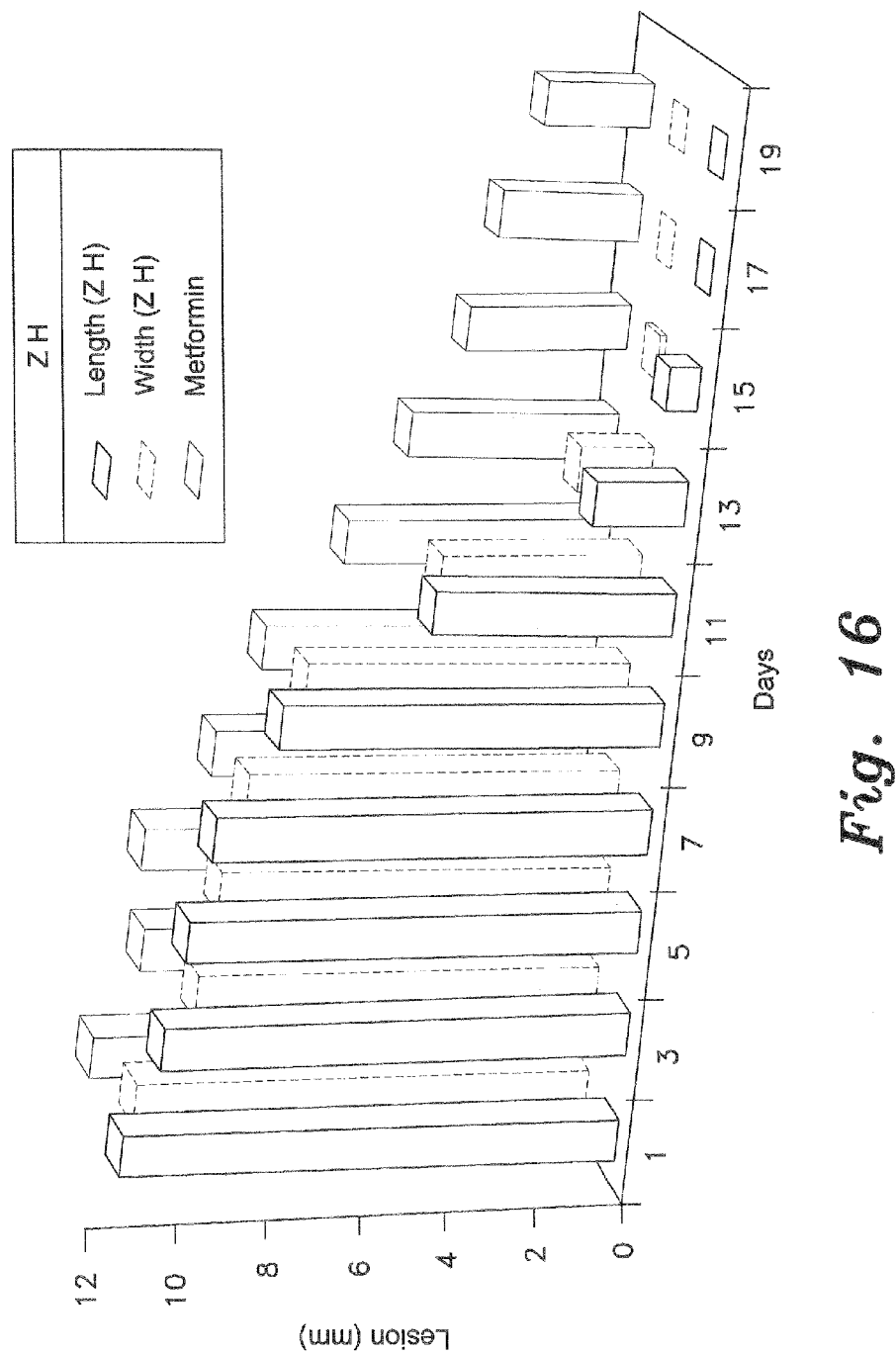
FIG. 16 is a chart comparing lesion size (mm) as a function of days for metformin, and for zinc oxide nanoparticles biosynthesized using *Trigonella foenum-graecum* extract.

Male Wistar rats weighing 200-250 gm were used for this study. The animals were fed with standard laboratory chow and had free access to water under well ventilated conditions of 12 hours day and 12 hours dark cycles. The animals were acclimatized to laboratory conditions prior to the experiment. The protocols were approved by the National Committee for Medical and Bio-ethics at our institute. The animals were handled according to standard protocols for the use of laboratory animals. The rats were made to fast 12 hours before the induction of diabetes. Thereafter, they were injected with streptozotocin (70 mg/kg, i.p.). This dose of streptozotocin induces diabetes in rats. Five days after injection the rats with fasting blood glucose higher than 150 nmole/L were considered diabetic and used for the experiment. Feeding was stopped 12 hours before blood sampling. The experimental groups (each group contains ten rats) were (1) Diabetic groups treated with metformin, which was used to control diabetes as a commercial drug; (2) diabetic group treated with *Cinnamomum cassia* (JF) as a control; and (3) Diabetic group treated with silver and gold nanoparticles synthesized by *Cinnamomum cassia*. Commercially available kits for the estimation of serum glucose were used. The gold and silver nanoparticles synthesized as described above were administered by topical application of the treatment was followed on the cutaneous diabetic wounds (daily dose). FIG. 11 shows the lesions (mm) as a function of the metformin and silver/gold nanocomposite synthesized by *Cinnamomum cassia* extract of the dosage described above. The initial lesions were made while the rats were anesthetized and using sanitized scissors. The lesion cut was made 1 cm×1 cm also the initial lesions were 10 mm±2 mm in the skin of rats. The graphs clearly illustrate that the rats treated with silver/gold nanocomposite synthesized by *Cinnamomum cassia* extract (SG JF) shows the greatest improvement in the size of the lesions, indicating that the diabetic wound healing is fastest. From the observation of the charts in FIGS. 11, 12, 13, 14, 15, 16, the silver/gold nanocomposite and zinc oxide nanoparticles synthesized from *Trigonella foenum-graecum* extract was much better and fastest in healing of the diabetic wound than silver/gold nanocomposite and zinc oxide nanoparticles synthesized from *Cinnamomum cassia* and *Solenostemma argel* extracts.

The examples describe synthesis of bimetallic nanoparticles of silver/gold nanocomposite together in the same sample that can be applied directly in the treatment of diabetes and healing the diabetic wound. Also the examples describe the synthesis of zinc oxide (ZnO) nanoparticles. It is contemplated that the compositions can be formulated as a cream or in the form of drops for topical application in the treatment of healing diabetic wound. There are several commercial benefits of the nanoparticles since these can be synthesized from low cost, local and available resources. Additionally, these can be scaled up and manufactured in large quantities for commercial use.

It is to be understood that the present invention is not limited to the embodiments described above, but encompasses any and all embodiments within the scope of the following claims.

We claim:

1. A method of treating cutaneous wounds in a diabetic patient using biosynthesized nanoparticles, comprising the step of administering to a patient in need thereof an effective amount of a composition containing zinc oxide nanoparticles biosynthesized by reduction in an aqueous plant extract to promote wound healing, wherein the aqueous plant extract comprises an aqueous extract of *Solenostemma argel* plant, further wherein the nanoparticles are rod-shaped, additionally wherein the step of administering the composition comprises topical application of the composition to the cutaneous wound.

2. The method of treating cutaneous wounds according to claim 1, wherein the effective amount comprises of the zinc oxide nanoparticles 400 mg per kilogram of body weight.

3. The method of treating cutaneous wounds according to claim 1, wherein the composition is formulated as a cream for topical administration.

4. The method of treating cutaneous wounds according to claim 1, wherein the composition is formulated as a suspension for topical administration as drops.

* * * * *